United States Patent [19]

Newman et al.

[11] Patent Number: 5,346,061
[45] Date of Patent: Sep. 13, 1994

[54] BIOSTABLE TREATMENT DELIVERY SYSTEM

[75] Inventors: Martin H. Newman, Sharon; Philip Sanfilippo, Natick, both of Mass.

[73] Assignee: Avitar, Inc., Canton, Mass.

[21] Appl. No.: 926,767

[22] Filed: Aug. 6, 1992

[51] Int. Cl.⁵ .................. B65D 25/08; A61B 19/02
[52] U.S. Cl. .................. 206/221; 206/828; 206/63.5; 424/400; 424/435
[58] Field of Search .............. 424/400, 435; 206/63.5, 206/221, 207, 205, 828, 210

[56] References Cited

U.S. PATENT DOCUMENTS

| | | | |
|---|---|---|---|
| 2,487,236 | 11/1949 | Greenberg | 206/47 |
| 3,608,566 | 9/1971 | Storandt | 206/63.5 |
| 3,762,540 | 10/1973 | Baumann et al. | 206/63.5 |
| 4,934,534 | 6/1990 | Wagner | 206/568 |
| 4,944,947 | 7/1990 | Newman | 424/435 |
| 5,086,915 | 2/1992 | Yoshima et al. | 206/205 |
| 5,176,251 | 1/1993 | Davis et al. | 206/205 |

Primary Examiner—Thurman K. Page
Assistant Examiner—Peter F. Kulkosky
Attorney, Agent, or Firm—Robert F. O'Connell

[57] ABSTRACT

A treatment delivery system which uses a flexible plastic outer container and a smaller, readily burstable, thin film plastic inner container fixedly positioned in the outer container. The inner container contains a treatment solution and a dry foam appliance is loosely placed within the inner container. When the inner container is burst by applying pressure to the outer container at a position which corresponds to the position of the inner container therein, the treatment solution comes into contact with the foam appliance so as to be absorbed by, and to wet the appliance. The wetted foam appliance can then be removed from the outer container for use.

9 Claims, 1 Drawing Sheet

BIOSTABLE TREATMENT DELIVERY SYSTEM

INTRODUCTION

This invention relates generally to treatment delivery systems and, more particularly, to a packaged system containing a treatment material and a separate treatment appliance which can be easily and readily combined in the packaged system prior to use.

BACKGROUND OF THE INVENTION

In the treatment of teeth and/or gums, it is desirable that the treatment material be effectively delivered to the teeth or gums so that such material is in an activated form when placed in contact with the teeth or gums. A suitable appliance useful for such purpose is described, for example, in U.S. Pat. No. 4,944,947 issued to M. H. Newman on Jul. 31, 1990. As described therein, a horseshoe-shaped, foamed polymer dental appliance has an aqueous treatment solution distributed therein so that when the appliance is positioned over the teeth and gums of a patient, the treatment solution is readily applied thereto. The appliance need only be left in the patient's mouth for several minutes in order for an effective treatment to take place. Such treatment solution may be, for example, a fluoride solution, a bleach solution, or any other effective treatment solution.

Normally, the treatment solution is added to the foamed polymer during manufacture of the appliance and the wetted appliance is then shipped in an hermetically sealed pouch, or bag, for subsequent opening and removal of the appliance for use on a patient. Alternatively, a dry vacuum-formed dental impression tray appliance can be shipped in one package or container and the treatment solution shipped in a suitable vial or other container, which is separate therefrom. A dentist, or dental hygienist, for example, then must open both containers and apply the treatment solution to the dry foam polymer appliance before applying it to the patient.

Neither of the above techniques is satisfactory. In the first approach, the treatment solution may be physically squeezed from the foam polymer appliance and the drug may degrade due to oxidation. The foam polymer appliance then contains a reduced amount thereof and the treatment effectiveness is reduced. In the second approach, the handling of both the appliance and the solution may contaminate them, and also is inconvenient and untidy. Furthermore, the application of solution to the appliance is often inefficiently performed so that its treatment effectiveness is also reduced.

It is desirable to devise a technique for handling a foam polymer appliance and a treatment solution in an antiseptic, easy-to-use, and efficient manner which assures a uniform distribution of solution throughout the foam polymer material so that the treatment effectiveness is maximized.

BRIEF SUMMARY OF THE INVENTION

In accordance with the invention, a foam polymer dental appliance is placed in an outer pouch, or container, which has therein a relatively smaller inner pouch, or container, containing a treatment solution which is to be distributed within the foam polymer material. The smaller treatment solution inner pouch is fixedly attached to and positioned within the outer container at a specified region thereof and the overall outer container is hermetically sealed once the foam polymer appliance and the treatment solution pouch are placed therein.

The treatment solution inner pouch is made of a material which can be readily burst when pressure is applied thereto so that, when the appliance is ready to be used, the user merely applies pressure to the outer surface of the outer container at the region thereof where the treatment solution pouch is fixedly located. Such pressure bursts the treatment solution inner pouch and causes the treatment solution to be released within the hermetically sealed outer container. The user can then manipulate the outer container so that the treatment solution comes into contact with the dry foam appliance and becomes readily absorbed into the foam polymer material and thereupon becomes effectively distributed throughout the wetted appliance. The user then opens the outer container so as to make the then wetted foam polymer appliance available for applying to a patient's teeth and gums.

DESCRIPTION OF THE INVENTION

Figure 1:
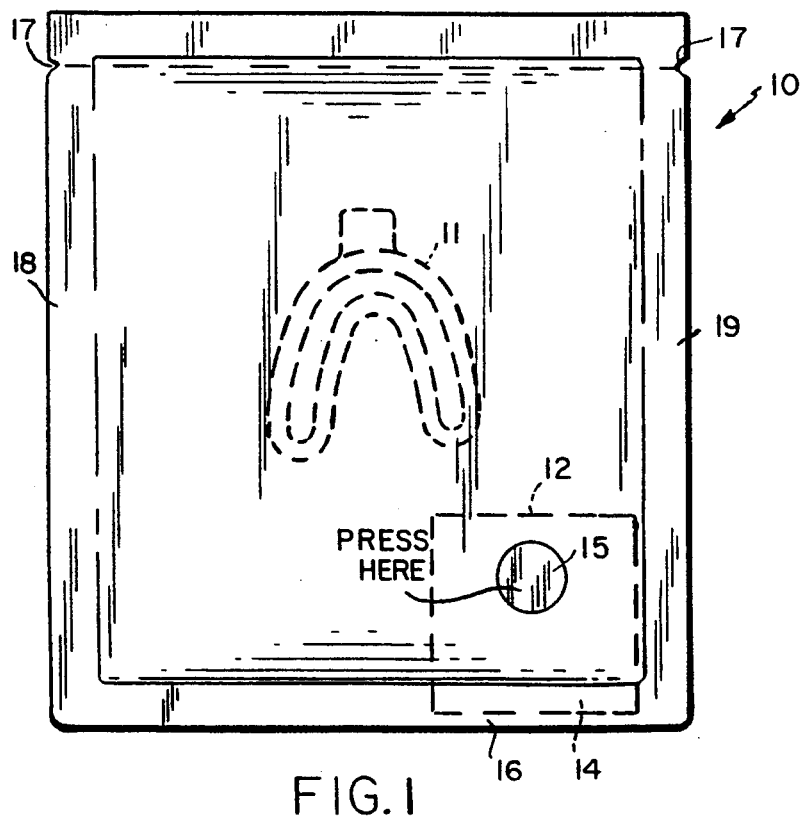
FIG. 1 shows a view of the exterior front surface of an overall container used in an embodiment of the invention.
Figure 2:
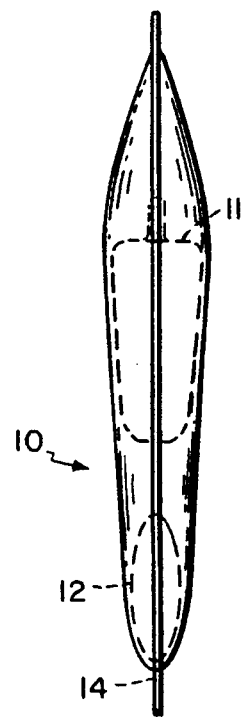
FIG. 2 shows an exterior side view of the container depicted in FIG. 1.
Figure 3:
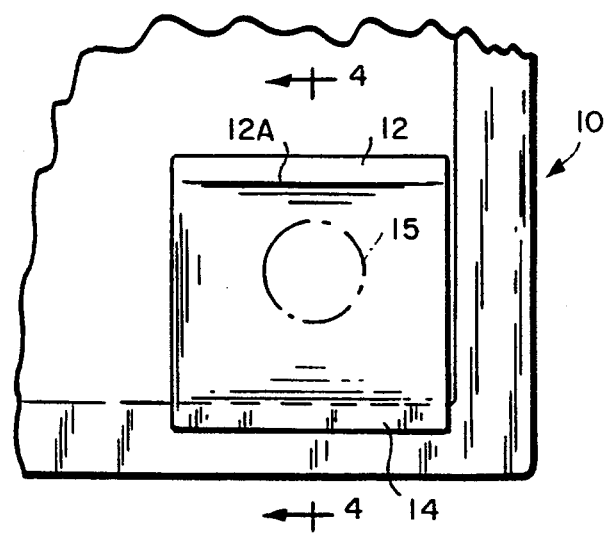
FIG. 3 shows a view of a portion of the exterior front surface of the container depicted in FIG. 1.
Figure 4:
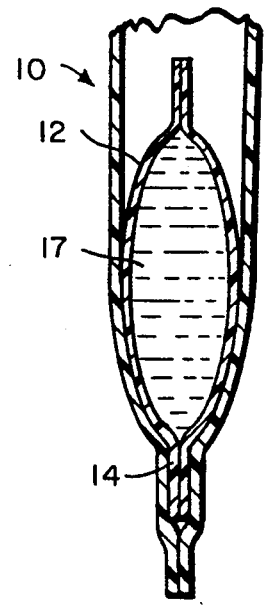
FIG. 4 shows a view in section of the portion of the container depicted in FIG. 3.

As can be seen in FIG. 1, an outer container 10, which in the particular embodiment being described is made of a suitable plastic material, such as an aluminum laminate material on the outer surface of a polyester film base having a polyethylene layer on the inner surface thereof, for example, is hermetically sealed around its four edges as shown. A foam polymer appliance 11, (shown by dashed lines) such as one of the type described in the aforementioned U.S. patent of M. Newman, is relatively loosely positioned within the interior of container 10. A treatment solution inner pouch 12 (shown by dashed lines), which is relatively smaller than container 10, is relative fixedly positioned at one corner of container 10 and has an edge 14 thereof positioned and sealed within the hermetic seal at edge 16 of outer container 10 so as to prevent undesired movement of inner pouch 12 within the container 10. Pouch 12 is positioned below a suitable exterior indicator 15, which is imprinted on the outer surface of container 10 in general registry with pouch 12. The indicator 15 may have a suitable legend, e.g., PRESS HERE, imprinted thereon, as shown.

Pouch 12 contains a treatment solution 17 which is to be distributed throughout foam polymer appliance 11. Such treatment solution may be a suitable fluoride solution, such as an aqueous solution of sodium fluoride, or may be a suitable bleaching, or whitening, solution, such as hydrogen peroxide. Pouch 12 is made of a thin film plastic material, such as a polyester, which is pre-scored along a pre-scored line 12A at the interior edge thereof opposite the edge which is sealed at edge 16 of outer container 10. The use of a thin film polyester material which is pre-scored allows for a relatively low burst strength so that when pressure is applied thereto, pouch 12 will readily burst at the pre-scored line 12A and make its contents readily available within the interior of container 10.

Thus, when a user, such as a dentist or dental hygienist, for example, desires to use the appliance on a patient, the user applies pressure firmly to the surface of container 10, which is placed on a surface, for example, at the indicator region 15 thereof, which action readily bursts pouch 12 so that the treatment solution 16 therein is released within the interior of container 10. The flexible outer container 10 can be manipulated by the user so as to make sure that the treatment solution comes into contact with the foam polymer appliance 11 where it is then absorbed and distributed throughout the foam polymer material.

The manipulation of container 10 after the pressure burst occurs, assures an effective spreading of the treatment solution within the container and into the foam material. Once the foam polymer appliance 11 is adequately wetted with the treatment solution, the container 10 can be opened by the user by tearing the container along a line between a pair of oppositely disposed notches 17 formed at opposite edges 18 and 19 of container 10. When the container is opened, the wetted appliance can be removed and inserted into a patient's mouth so that the treatment can take place, as discussed in the previously mentioned Newman U.S. patent.

While the embodiment of the invention disclosed above represents a preferred embodiment thereof, modifications thereto may occur to those in the art within the spirit and scope of the invention. Hence, the invention is not to be construed as limited thereto, except as defined by the appended claims.

What is claimed is:

1. A treatment delivery system comprising a readily openable hermetically and completely sealed flexible plastic outer container forming a single first chamber;
   a completely sealed and flexible plastic inner container, forming a single second chamber, which is smaller than said outer container and is fixedly positioned within the single first chamber of said outer container so as to be completely enclosed therein, said inner container containing a treatment solution and being made of a thin film plastic material so that it can be readily burst upon the application of pressure thereto;
   a dry foam element placed within said outer container;
   means on said outer container for indicating the position of said inner container within said outer container so that, when pressure is applied to the outer container at said indicated position, the inner container bursts and said treatment solution comes into contact with said dry foam element so as to wet said foam element with the treatment solution, whereby the wetted foam element is available for delivery of said treatment solution when the outer container is open.

2. A treatment delivery system in accordance with claim 1 wherein said flexible outer container is made of polyester film base having an aluminum laminate on one surface thereof and a polyethylene layer on the opposite surface thereof.

3. A treatment delivery system in accordance with claim 1 wherein said inner container is made of a thin film polyester plastic material.

4. A treatment delivery system in accordance with claim 3 wherein said inner container is pre-scored along an edge thereof.

5. A treatment delivery system in accordance with claim 1 wherein said indicating means is a legend imprinted on said outer container in substantial registry with the position of said inner container within the outer container.

6. A treatment delivery system in accordance with claim 1 wherein said dry foam element is loosely placed within said outer container so that, when said treatment solution is present after the inner container is burst, said outer container can be manipulated to assure that the foam element therein is thoroughly wetted with said treatment solution.

7. A treatment delivery system in accordance with claim 1 wherein said dry foam element is a dental appliance and said treatment solution is dental treatment solution.

8. A treatment delivery system in accordance with claim 7 wherein said dental treatment solution is a fluoride solution.

9. A treatment delivery system in accordance with claim 7 wherein said dental treatment solution is a bleaching solution.

* * * * *